US00PP29414P3

(12) United States Plant Patent
Pieters et al.

(10) Patent No.: US PP29,414 P3
(45) Date of Patent: Jun. 19, 2018

(54) ***GUZMANIA* PLANT NAMED 'SENSATION'**

(50) Latin Name: *Guzmania hybrida*
Varietal Denomination: Sensation

(71) Applicants: Luc Pieters, Laarne (BE); Caroline De Meyer, Laarne (BE)

(72) Inventors: Luc Pieters, Laarne (BE); Caroline De Meyer, Laarne (BE)

( * ) Notice: Subject to any disclaimer, the term of this patent is extended or adjusted under 35 U.S.C. 154(b) by 0 days. days.

(21) Appl. No.: 14/999,692

(22) Filed: Jun. 16, 2016

(65) Prior Publication Data

US 2017/0367244 P1 Dec. 21, 2017

(51) Int. Cl.
*A01H 5/02* (2018.01)

(52) U.S. Cl.
USPC ..... Plt./371
CPC ..... *A01H 5/02* (2013.01)

(58) Field of Classification Search
USPC ..... Plt./371
CPC ..... A01H 5/02; A01H 5/00
See application file for complete search history.

(56) References Cited

PUBLICATIONS

Upov Pluto Plant Variety Database Jul. 13, 2017 for *Guzmania* Primavera retrieved on Jul. 19, 2017, retrieved from the internet at <http://www.upov.int/pluto/en/index.jsp> one page.*

* cited by examiner

*Primary Examiner* — June Hwu
(74) *Attorney, Agent, or Firm* — C. A. Whealy

(57) ABSTRACT

A new and distinct cultivar of *Guzmania* plant named 'Sensation', characterized by its upright and outwardly arching growth habit; broad inflorescences with showy dark red-colored bracts; and good postproduction longevity.

2 Drawing Sheets

Botanical designation: *Guzmania hybrida.*
Cultivar denomination: 'SENSATION'.

BACKGROUND OF THE INVENTION

The present invention relates to a new and distinct cultivar of *Guzmania* plant, botanically known as *Guzmania hybrida* and hereinafter referred to by the name 'Sensation'.

The new *Guzmania* plant is a product of a planned breeding program conducted by the Inventors in Laarne, Belgium. The objective of the breeding program is to create new *Guzmania* plants having unique bract colors and enhanced postproduction longevity.

The new *Guzmania* originated from a cross-pollination made by the Inventors in January, 2005 in Laarne, Belgium of *Guzmania hybrida* 'Denise', not patented, as the female, or seed, parent with an unnamed proprietary selection of *Guzmania cardinalis*×*Guzmania variegata*, not patented, as the male, or pollen, parent. The new *Guzmania* plant was discovered and selected by the Inventors as a single flowering plant from within the progeny of the stated cross-pollination in a controlled environment in Laarne, Belgium in November, 2008.

Asexual reproduction of the new *Guzmania* plant by meristem culture in a controlled environment in Laarne, Belgium since March, 2010 has shown that the unique features of this new *Guzmania* plant are stable and reproduced true to type in successive generations.

SUMMARY OF THE INVENTION

Plants of the new *Guzmania* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sensation'. These characteristics in combination distinguish 'Sensation' as a new and distinct *Guzmania* plant:

1. Upright and outwardly arching growth habit.
2. Broad inflorescences with showy dark red-colored bracts.
3. Good postproduction longevity.

Plants of the new *Guzmania* can be compared to plants of the female parent, 'Denise'. Plants of the new *Guzmania* differ primarily from plants of 'Denise' in plant size as plants of the new *Guzmania* have shorter flower scapes than plants of 'Denise'. In addition, plants of the new *Guzmania* and 'Denise' differ in bract color as plants of 'Denise' have lighter red-colored bracts.

Plants of the new *Guzmania* can be compared to plants of the male parent selection. Plants of the new *Guzmania* differ primarily from plants of the male parent selection in plant size as plants of the new *Guzmania* have longer flower scapes than plants of the male parent selection.

Plants of the new *Guzmania* can also be compared to plants of *Guzmania* Ruiz & Pav. 'Primavera', not patented. Plants of the new *Guzmania* differ primarily from plants of 'Primavera' in flower and scape bract color as plants of 'Primavera' have yellow-colored flower and scape bracts.

Plants of the new *Guzmania* can be compared to plants of *Guzmania hybrida* 'Calypso', not patented. In side-by-side comparisons, plants of the new *Guzmania* and 'Calypso' differ in the following characteristics:

1. Plants of the new *Guzmania* have longer flower scapes than plants of 'Calypso'.
2. Plants of the new *Guzmania* and 'Calypso' differ in bract color as plants of 'Calypso' have lighter red-colored bracts.

BRIEF DESCRIPTION OF THE PHOTOGRAPHS

The accompanying colored photographs illustrate the overall appearance of the new *Guzmania* plant showing the colors as true as it is reasonably possible to obtain in colored reproductions of this type. Colors in the photographs may differ slightly from the color values cited in the detailed botanical description which accurately describe the colors of the new *Guzmania* plant.

The photograph on the first sheet comprises a side perspective view of a typical flowering plant of 'Sensation' grown in a container.

The photograph on the second sheet is a close-up view of a typical inflorescence of 'Sensation'.

DETAILED BOTANICAL DESCRIPTION

The aforementioned photographs and following observations, measurements and values describe plants grown during the winter in 12-cm containers in a glass-covered greenhouse in Laarne, Belgium and under cultural practices typical of commercial *Guzmania* production. During the production of the plants, day temperatures ranged from 21° C. to 30° C., night temperatures ranged from 20° C. to 21° C. and maximum light levels were 18,000 lux. Plants were three years old when the photographs and description were taken. In the following description, color references are made to The Royal Horticultural Society Colour Chart, 2015 Edition, except where general terms of ordinary dictionary significance are used.

Botanical classification: *Guzmania hybrida* 'Sensation'.

Parentage:

*Female, or seed, parent.*—*Guzmania hybrida* 'Denise', not patented.

*Male, or pollen, parent.*—Unnamed proprietary selection of *Guzmania cardinalis*×*Guzmania variegata*, not patented.

Propagation:

*Type.*—By meristem culture.

*Root description.*—Thick, fleshy; creamy white in color.

*Rooting habit.*—Medium density.

Plant description:

*Plant and growth habit.*—Upright and outwardly arching plant habit; broad inverted triangle; basal rosette of outwardly curved strap-like leaves affixed in tight spiral ranks; terminal inflorescence on an upright scape emerging from the center of the basal rosette; moderately vigorous growth habit.

*Plant height, soil surface to top of foliar plane.*—About 32.4 cm.

*Plant height, soil surface to top of inflorescence.*—About 48.1 cm.

*Plant diameter or spread.*—About 73.8 cm.

Leaf description:

*Arrangement.*—Basal rosette, spiral phyllotaxis; leaves sessile.

*Length.*—About 47.1 cm.

*Width.*—About 4.8 cm.

*Shape.*—Ligulate; slightly concave.

*Apex.*—Apiculate.

*Base.*—Sheathing.

*Margin.*—Entire.

*Aspect.*—Leaves curved outward over their length and arching downward towards the apex.

*Texture and luster, upper and lower surfaces.*—Leathery, stiff; smooth, glabrous; glossy.

*Venation.*—Parallel.

*Color.*—Developing leaves, upper and lower surfaces: Close to 146A. Fully expanded leaves, upper surface: Close to between NN137A and 147A; venation, similar to lamina. Fully expanded leaves, lower surface: Close to 146A; venation, similar to lamina.

*Leaf sheath.*—Length: About 10.7 cm. Width: About 8.3 cm. Texture and luster, upper surface: Smooth, glabrous; slightly glossy. Texture and luster, lower surface: Smooth, glabrous; moderately glossy. Color, upper surface: Close to 161A to 161B. Color, lower surface: Close to 161A; towards the base, close to 166A to 166B.

Inflorescence description:

*Inflorescence form.*—Terminal inflorescences with showy bracts; inflorescences supported on erect and strong scapes.

*Inflorescence length.*—About 10.9 cm.

*Inflorescence width.*—About 20.6 cm.

*Fragrance.*—None detected.

*Inflorescence longevity.*—Inflorescences of the new *Guzmania* are long-lasting; bract coloration is maintained for about four to five months; inflorescences persistent.

*Natural flowering season.*—Plants of the new *Guzmania* flower naturally from spring until the autumn; plants begin flowering about three to four months.

*Flowers.*—Appearance and quantity: Single small flowers with about twelve flowers developing per inflorescence. Diameter: About 4 mm. Depth (height): About 1.7 cm.

*Flower buds.*—Length: About 1.3 cm. Diameter: About 3.5 mm. Shape: Lanceolate. Texture and luster: Smooth, glabrous; glossy. Color: Close to 15A and 15B; completely covered with a transparent bract, close to 153D.

*Petals.*—Quantity per flower: Three. Length: About 1.6 cm. Width: About 4 mm. Shape: Narrowly oblong. Apex: Bluntly acute. Base: Broadly cuneate. Margin: Entire. Texture and luster, upper surface: Smooth, glabrous; matte. Texture and luster, lower surface: Smooth, glabrous; slightly glossy. Color, immature and mature, upper surface: Close to 15A; towards the base, close to 1A and 1B. Color, immature and mature, lower surface: Close to 15A; towards the base, close to 1A and 1B.

*Sepals.*—Quantity per flower: Three. Length: About 2.6 cm. Width: About 5 mm. Shape: Narrowly oblong to lanceolate. Apex: Acute. Base: Broadly cuneate. Texture and luster, upper surface: Smooth, glabrous; moderately glossy. Texture and luster, lower surface: Smooth, glabrous; slightly glossy. Color, immature, upper and lower surfaces: Close to 155A; towards the apex, close to 160C and 160D. Color, mature, upper and lower surfaces: Close to 155A; towards the apex, close to 160C and 160D.

*Reproductive organs.*—Stamens: Quantity per flower: Three. Filament length: About 9 mm. Filament color:

Close to 157A. Anther length: About 7 mm. Anther shape: Narrowly sagittate. Anther color: Close to 155A. Pollen: None observed. Pistils: Quantity per flower: One. Pistil length: About 9 mm. Style length: About 7.5 cm. Style color: Close to 4C. Stigma diameter: About 1 mm. Stigma shape: Clavate, three-lobed. Stigma color: Close to 5C. Ovary color: Close to 145D.

*Scapes*.—Length: About 38.9 cm. Diameter: About 9 mm. Strength: Strong. Aspect: Erect. Texture and luster: Smooth, glabrous; slightly glossy. Color: Close to between 145C and 150C.

*Flower bracts*.—Length: About 4.5 cm. Width: About 1.2 cm. Shape: Oblong. Apex: Bluntly acute. Base: Broadly cuneate. Margins: Entire. Texture, upper and lower surfaces: Smooth, glabrous. Color: When developing and fully developed, upper surface: Close to 34A to 34C; towards the base, close to 155A to 155C. When developing and fully developed, lower surface: Close to 34B to 34C; towards the base, close to 155A to 155B.

*Scape bracts*.—Length: About 10.7 cm. Width: About 3.1 cm. Shape: Ligulate. Apex: Acuminate. Base: Sheathing the scape. Margins: Entire. Texture, upper and lower surfaces: Smooth, glabrous. Color: When developing, upper surface: Close to N45A. When developing, lower surface: Close to 45A. Fully developed, upper surface: Close to N45A; apex, close to 137A. Fully developed, lower surface: Close to 45A; apex, close to 146A.

Temperature tolerance: Plants of the new *Guzmania* have been observed to tolerate high temperatures about 40° C. and to be suitable for USDA Hardiness Zones 10 to 12.

Disease & pest resistance: Plants of the new *Guzmania* have not been observed to resistant to pathogens and pests common to *Guzmania* plants.

It is claimed:

1. A new and distinct *Guzmania* plant named 'Sensation' as illustrated and described.

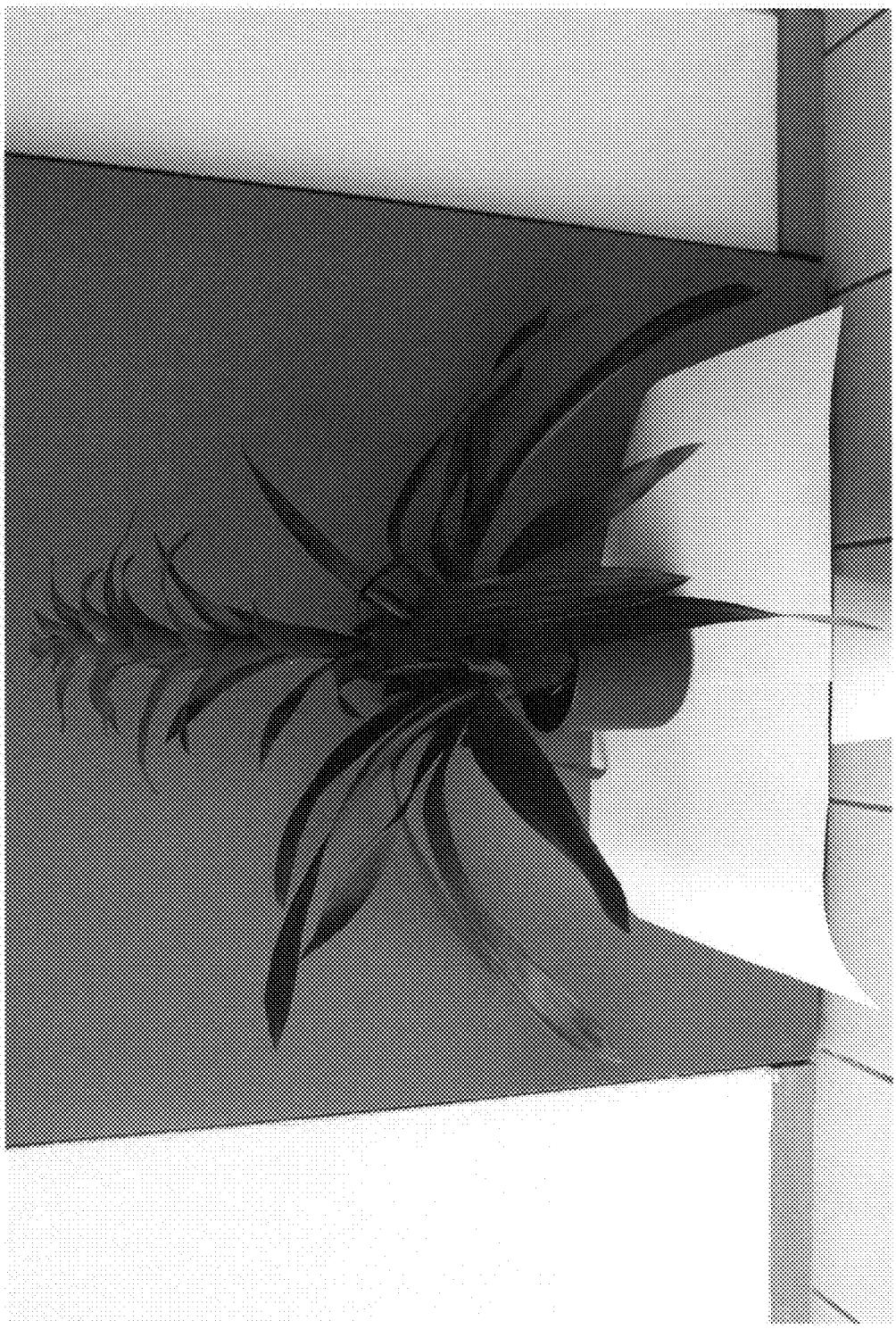

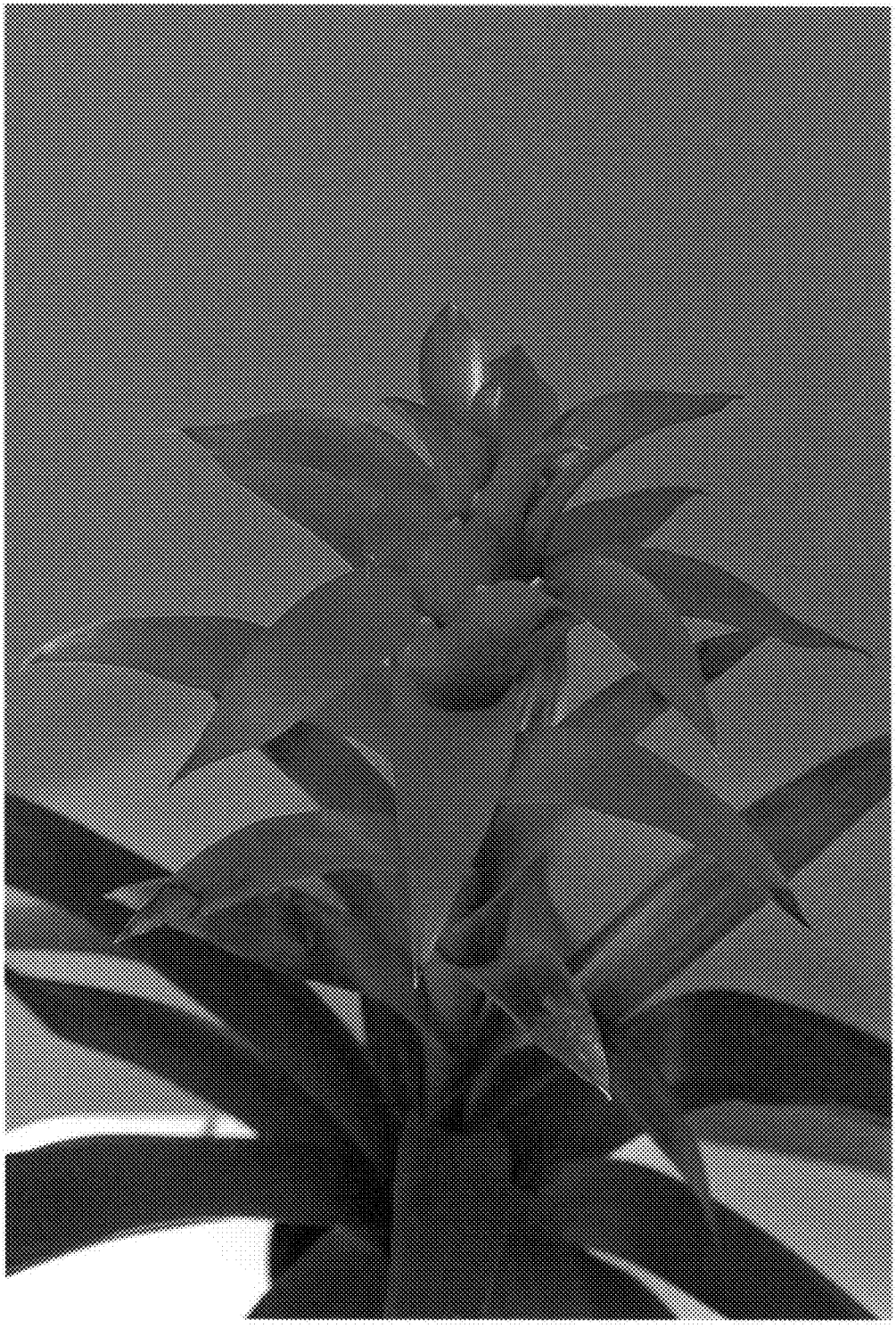

* * * * *